(12) United States Patent
Surnilla et al.

(10) Patent No.: US 8,763,594 B2
(45) Date of Patent: *Jul. 1, 2014

(54) HUMIDITY AND FUEL ALCOHOL CONTENT ESTIMATION

(71) Applicant: Ford Global Technologies, LLC, Dearborn, MI (US)

(72) Inventors: Gopichandra Surnilla, West Bloomfield, MI (US); Richard E. Soltis, Saline, MI (US); Dan A. Makled, Dearborn, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/972,747

(22) Filed: Aug. 21, 2013

(65) Prior Publication Data
US 2013/0333677 A1    Dec. 19, 2013

Related U.S. Application Data

(63) Continuation-in-part of application No. 13/953,621, filed on Jul. 29, 2013, now Pat. No. 8,731,806, which is a continuation of application No. 12/781,328, filed on May 17, 2010, now Pat. No. 8,495,996, which is a continuation-in-part of application No. 12/631,013, filed on Dec. 4, 2009, now Pat. No. 8,522,760.

(51) Int. Cl.
*F02D 41/00* (2006.01)

(52) U.S. Cl.
USPC .................................. 123/703; 123/27 GE (58) Field of Classification Search
USPC ............. 123/1 A, 27 GE, 299, 479, 525, 575, 123/693, 695, 698, 703; 701/103; 60/726, 60/299; 73/114.69, 114.71
See application file for complete search history.

(56) References Cited

U.S. PATENT DOCUMENTS

| | | | |
|---|---|---|---|
| 4,915,080 A | 4/1990 | Nakaniwa et al. | |
| 4,945,882 A | 8/1990 | Brown et al. | |
| 4,953,390 A | 9/1990 | Krempl et al. | |
| 4,957,087 A | 9/1990 | Ota | |
| 4,982,709 A * | 1/1991 | Oota | 123/339.12 |
| 4,993,386 A | 2/1991 | Ozasa et al. | |
| 5,145,566 A | 9/1992 | Logothetis et al. | |
| 5,195,497 A | 3/1993 | Yoshida et al. | |
| 5,253,631 A * | 10/1993 | Curran | 123/696 |
| 5,255,661 A | 10/1993 | Nankee, II et al. | |

(Continued)

OTHER PUBLICATIONS

Surnilla, Gopichandra et al., "Methods and Systems for Humidity Detection via an Exhaust Gas Sensor," U.S. Appl. No. 13/973,155, filed Aug. 22, 2013, 41 pages.

*Primary Examiner* — John Kwon
*Assistant Examiner* — Johnny H Hoang
(74) *Attorney, Agent, or Firm* — Julia Voutyras; Alleman Hall McCoy Russell & Tuttle LLP (57) ABSTRACT

Methods and systems for an engine system including an exhaust gas sensor are disclosed. In one example, under a first engine fueling condition, an air-fuel ratio correction factor is determined based on an expected air-fuel ratio and an actual air-fuel ratio. During a second engine fueling condition and a third engine non-fueling condition, fuel alcohol content and ambient humidity, respectively, are determined based on the exhaust gas sensor and corrected based on the air-fuel ratio correction factor.

20 Claims, 7 Drawing Sheets

(56) References Cited

U.S. PATENT DOCUMENTS

| | | | |
|---|---|---|---|
| 5,291,673 A | 3/1994 | Hamburg et al. | |
| 5,400,762 A | 3/1995 | Fodale et al. | |
| 5,623,824 A * | 4/1997 | Yukawa et al. | 60/276 |
| 5,735,245 A | 4/1998 | Kubesh et al. | |
| 5,850,824 A | 12/1998 | Seitz et al. | |
| 5,881,703 A | 3/1999 | Nankee, II et al. | |
| 6,227,033 B1 * | 5/2001 | Kainz | 73/23.32 |
| 6,644,097 B2 | 11/2003 | Davey et al. | |
| 6,918,362 B2 * | 7/2005 | Cullen | 123/90.15 |
| 7,209,826 B2 | 4/2007 | Abe et al. | |
| 7,694,508 B2 | 4/2010 | Iida et al. | |
| 7,826,957 B2 * | 11/2010 | Fabien | 701/103 |
| 2003/0042151 A1 * | 3/2003 | Ando et al. | 205/781 |
| 2004/0098967 A1 * | 5/2004 | Cook et al. | 60/274 |
| 2005/0252771 A1 * | 11/2005 | Wiedenmann et al. | 204/426 |
| 2007/0056860 A1 * | 3/2007 | Inagaki et al. | 205/784.5 |
| 2007/0119422 A1 * | 5/2007 | Lewis et al. | 123/431 |
| 2007/0215110 A1 * | 9/2007 | Stein et al. | 123/431 |
| 2008/0196490 A1 * | 8/2008 | Fukagai et al. | 73/114.72 |
| 2009/0084172 A1 * | 4/2009 | Fukagai et al. | 73/114.72 |
| 2010/0236532 A1 * | 9/2010 | Xiao et al. | 123/677 |
| 2010/0300418 A1 * | 12/2010 | Aoki | 123/703 |
| 2011/0132340 A1 | 6/2011 | Soltis | |
| 2011/0132342 A1 | 6/2011 | Soltis et al. | |
| 2012/0324864 A1 | 12/2012 | Krengel et al. | |

\* cited by examiner

HUMIDITY AND FUEL ALCOHOL CONTENT ESTIMATION

CROSS REFERENCE TO RELATED APPLICATIONS

The present application is a continuation-in-part of U.S. patent application Ser. No. 13/953,621 filed on Jul. 29, 2013, which is a continuation of U.S. patent application Ser. No. 12/781,328 filed on May 17, 2010, now U.S. Pat. No. 8,495,996, which is a continuation-in-part of U.S. patent application Ser. No. 12/631,013 filed on Dec. 4, 2009; and the present application is a continuation-in-part of U.S. patent application Ser. No. 12/631,013 filed on Dec. 4, 2009 the entire contents of each of which are hereby incorporated by reference for all purposes.

TECHNICAL FIELD

The present application relates generally to an exhaust gas sensor coupled to an exhaust system of an internal combustion engine.

BACKGROUND AND SUMMARY

Exhaust gas sensors may be operated to provide indications of various exhaust gas constituents. For example, U.S. Pat. No. 5,145,566 describes detecting water content in the exhaust gas. Water content estimated using an exhaust gas oxygen sensor may be used to infer an ambient humidity during engine operation. In still other approaches, the water content may be used to infer a fuel alcohol content of a fuel burned in the engine.

However the inventors herein have identified potential issues with such an approach. Specifically, changes in exhaust air-fuel ratio can impact the output of the oxygen sensor, confounding the inferred results. Specifically, when the exhaust fuel ratio is richer than stoichiometry, the pumping current output by the oxygen sensor upon application of a voltage may be higher than expected. The error in pumping current results in an error in a corresponding humidity and fuel alcohol content estimation. Since humidity and fuel alcohol content are factors in determining engine operating parameters, such as injection amount, EGR amount, etc., errors in humidity and/or fuel alcohol content estimation can translate into degraded engine performance. In some approaches, the air-fuel ratio may be controlled to a target air-fuel ratio and the water content estimation may be performed only when the air-fuel ratio is at the target value. However, this not only relies on accurate air-fuel ratio control but also requires fuel adaptation to be completed before the water content can be estimated. As a result, during lengthy fuel adaptations, the water content estimation is delayed.

Thus, in one example, some of the above issues may be addressed by a method for an engine comprising, during a first engine fueling condition, applying a first voltage to an exhaust gas sensor, and learning an air-fuel ratio correction factor based on a sensor output. Further, during a second engine fueling condition following the first fueling condition, alternating between applying first and second voltages to the sensor, and estimating an injected fuel alcohol content based on sensor outputs at the first and second voltages and the learned correction factor.

Thus, in one example, the sensor outputs may be corrected to compensate for changes in air-fuel ratio. Specifically, responsive to application of the first and second voltages, first and second pumping currents may be generated. The first pumping current may be indicative of an amount of oxygen in a sample gas while the second pumping current may be indicative of the amount of oxygen in the sample gas plus an amount of oxygen contained in water molecules in the sample gas. The first and second pumping currents may then be corrected based on deviations of an expected air-fuel ratio (at which the engine is thought to be operating) from an estimated air-fuel ratio (at which the engine is actually operating). The corrected values may then be used to compute a water content, and infer an ambient humidity and an alcohol content of burned fuel with higher accuracy and reliability.

In this way, exhaust water content estimation and fuel alcohol content determination can be performed rapidly and accurately without requiring air-fuel ratio control. Specifically, the estimation can be performed without requiring the air-fuel ratio to be accurately controlled to a target value. In other words, the approach corrects for the air-fuel ratio being different from the target rather than controlling the air-fuel ratio to the target. As such, this allows water and alcohol content estimation to be performed without requiring fuel adaptation to be completed for accurate open-loop fueling. The inventors have also recognized that by using the same exhaust gas sensor to determine ambient humidity (for example, when the engine is operating without fueling, such as during a deceleration fuel shut-off), fuel alcohol content (for example, during a condition other than after a fuel tank re-fill), and an exhaust gas air-fuel ratio correction factor (for example, when the engine is operating fueled), component reduction benefits can be achieved.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

The following description relates to a method for determining an amount of alcohol in a fuel mixture (e.g., ethanol and gasoline) based on outputs from an exhaust gas sensor, such as an oxygen sensor. The exhaust gas sensor may be used to determine an amount of water in a sample gas which represents an amount of water in the exhaust gas at the time of the measurement. For example, a first voltage may be applied to the sensor to determine an air-fuel ratio error based on an expected air-fuel ratio and an actual air-fuel ration. Then, first and second voltages may be alternately applied to the sensor to generate first and second pumping currents (e.g., sensor outputs). Under engine non-fueling conditions such as deceleration fuel shut-off, the outputs of the sensor may be corrected based on the air-fuel ratio correction factor and used to generate an indication of ambient humidity. During engine fueling conditions, the sensor outputs may be corrected based on the air-fuel ratio correction factor and used with the ambient humidity to identify an amount of water in the exhaust which is proportional to the amount of alcohol in the fuel mixture. In one example, engine operating parameters such as spark timing and/or fuel injection amount may be adjusted based on the detected amount of alcohol in the fuel. In this manner, engine performance, fuel economy, and/or emissions may be maintained or improved despite the varying amounts of alcohol in the fuel.

Figure 1:
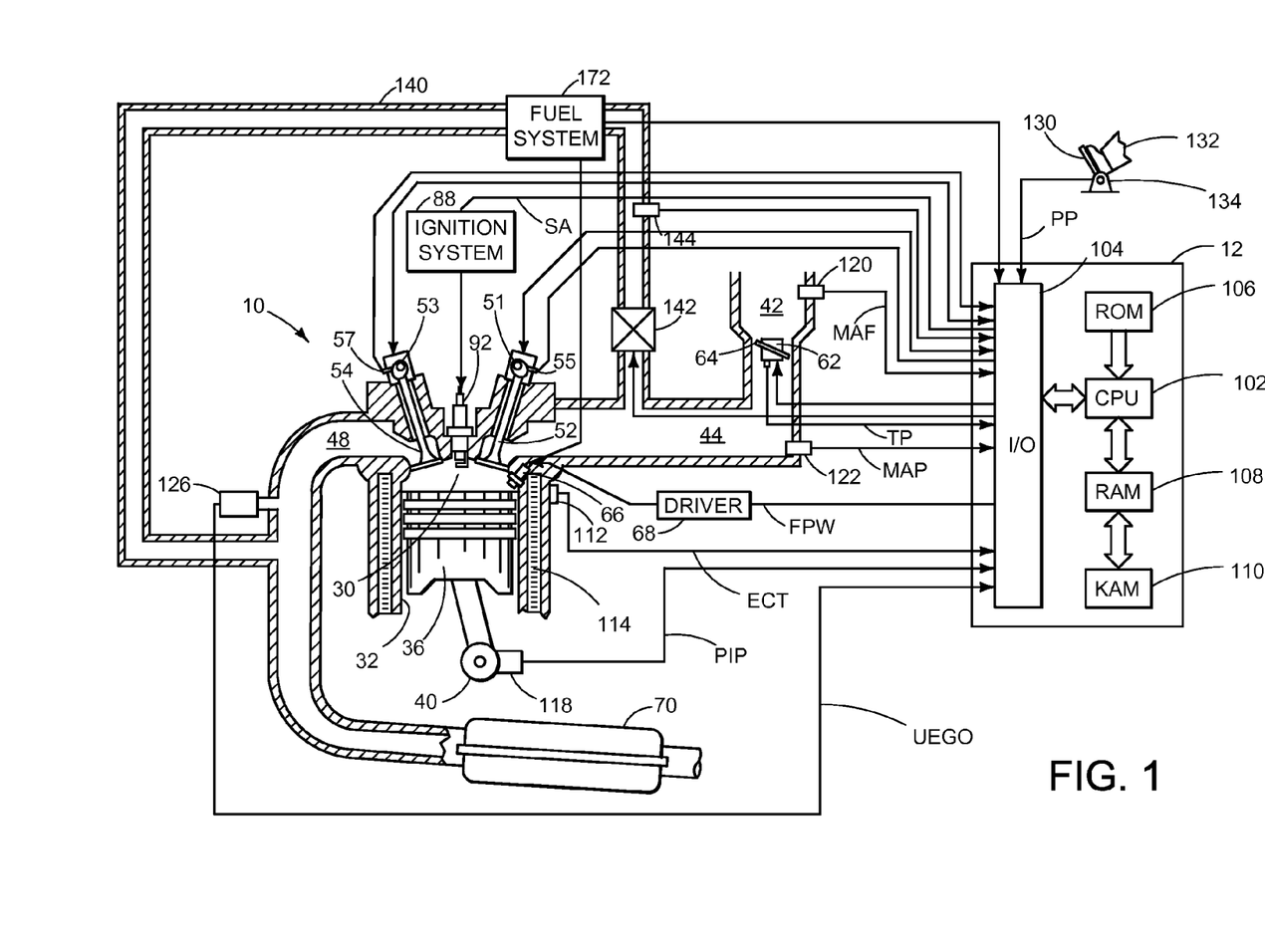
FIG. 1 shows a schematic diagram of an engine including an exhaust system and an exhaust gas sensor.

Referring now to FIG. 1, a schematic diagram showing one cylinder of multi-cylinder engine 10, which may be included in a propulsion system of an automobile, is illustrated. Engine 10 may be controlled at least partially by a control system including controller 12 and by input from a vehicle operator 132 via an input device 130. In this example, input device 130 includes an accelerator pedal and a pedal position sensor 134 for generating a proportional pedal position signal PP. Combustion chamber (i.e., cylinder) 30 of engine 10 may include combustion chamber walls 32 with piston 36 positioned therein. Piston 36 may be coupled to crankshaft 40 so that reciprocating motion of the piston is translated into rotational motion of the crankshaft. Crankshaft 40 may be coupled to at least one drive wheel of a vehicle via an intermediate transmission system. Further, a starter motor may be coupled to crankshaft 40 via a flywheel to enable a starting operation of engine 10.

Combustion chamber 30 may receive intake air from intake manifold 44 via intake passage 42 and may exhaust combustion gases via exhaust passage 48. Intake manifold 44 and exhaust passage 48 can selectively communicate with combustion chamber 30 via respective intake valve 52 and exhaust valve 54. In some embodiments, combustion chamber 30 may include two or more intake valves and/or two or more exhaust valves.

In this example, intake valve 52 and exhaust valves 54 may be controlled by cam actuation via respective cam actuation systems 51 and 53. Cam actuation systems 51 and 53 may each include one or more cams and may utilize one or more of cam profile switching (CPS), variable cam timing (VCT), variable valve timing (VVT), and/or variable valve lift (VVL) systems that may be operated by controller 12 to vary valve operation. The position of intake valve 52 and exhaust valve 54 may be determined by position sensors 55 and 57, respectively. In alternative embodiments, intake valve 52 and/or exhaust valve 54 may be controlled by electric valve actuation. For example, cylinder 30 may alternatively include an intake valve controlled via electric valve actuation and an exhaust valve controlled via cam actuation including CPS and/or VCT systems.

In some embodiments, each cylinder of engine 10 may be configured with one or more fuel injectors for providing fuel thereto. As a non-limiting example, cylinder 30 is shown including one fuel injector 66. Fuel injector 66 is shown coupled directly to cylinder 30 for injecting fuel directly therein in proportion to the pulse width of signal FPW received from controller 12 via electronic driver 68. In this manner, fuel injector 66 provides what is known as direct injection (hereafter also referred to as "DI") of fuel into combustion cylinder 30.

It will be appreciated that in an alternate embodiment, injector 66 may be a port injector providing fuel into the intake port upstream of cylinder 30. It will also be appreciated that cylinder 30 may receive fuel from a plurality of injectors, such as a plurality of port injectors, a plurality of direct injectors, or a combination thereof.

Fuel tank in fuel system 172 may hold fuels with different fuel qualities, such as different fuel compositions. These differences may include different alcohol content, different octane, different heats of vaporization, different fuel blends, and/or combinations thereof etc. The engine may use an alcohol containing fuel blend such as E85 (which is approximately 85% ethanol and 15% gasoline) or M85 (which is approximately 85% methanol and 15% gasoline). Alternatively, the engine may operate with other ratios of gasoline and ethanol stored in the tank, including 100% gasoline and 100% ethanol, and variable ratios therebetween, depending on the alcohol content of fuel supplied by the operator to the tank. Moreover, fuel characteristics of the fuel tank may vary frequently. In one example, a driver may refill the fuel tank with E85 one day, and E10 the next, and E50 the next. As such, based on the level and composition of the fuel remaining in the tank at the time of refilling, the fuel tank composition may change dynamically.

The day to day variations in tank refilling can thus result in frequently varying fuel composition of the fuel in fuel system 172, thereby affecting the fuel composition and/or fuel quality delivered by injector 66. The different fuel compositions injected by injector 166 may herein be referred to as a fuel type. In one example, the different fuel compositions may be qualitatively described by their research octane number (RON) rating, alcohol percentage, ethanol percentage, etc.

It will be appreciated that while in one embodiment, the engine may be operated by injecting the variable fuel blend via a direct injector, in alternate embodiments, the engine may be operated by using two injectors and varying a relative amount of injection from each injector. It will be further appreciated that when operating the engine with a boost from a boosting device such as a turbocharger or supercharger (not shown), the boosting limit may be increased as an alcohol content of the variable fuel blend is increased.

Continuing with FIG. 1, intake passage 42 may include a throttle 62 having a throttle plate 64. In this particular example, the position of throttle plate 64 may be varied by controller 12 via a signal provided to an electric motor or actuator included with throttle 62, a configuration that is commonly referred to as electronic throttle control (ETC). In this manner, throttle 62 may be operated to vary the intake air provided to combustion chamber 30 among other engine cylinders. The position of throttle plate 64 may be provided to controller 12 by throttle position signal TP. Intake passage 42 may include a mass air flow sensor 120 and a manifold air pressure sensor 122 for providing respective signals MAF and MAP to controller 12.

Ignition system 88 can provide an ignition spark to combustion chamber 30 via spark plug 92 in response to spark advance signal SA from controller 12, under select operating modes. Though spark ignition components are shown, in some embodiments, combustion chamber 30 or one or more other combustion chambers of engine 10 may be operated in a compression ignition mode, with or without an ignition spark.

Exhaust gas sensor 126 is shown coupled to exhaust passage 48 upstream of emission control device 70. Sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a $NO_x$, HC, or CO sensor. Emission control device 70 is shown arranged along exhaust passage 48 downstream of exhaust gas sensor 126. Device 70 may be a three way catalyst (TWC), $NO_x$ trap, various other emission control devices, or combinations thereof. In some embodiments, during operation of engine 10, emission control device 70 may be periodically reset by operating at least one cylinder of the engine within a particular air/fuel ratio.

Further, in the disclosed embodiments, an exhaust gas recirculation (EGR) system may route a desired portion of exhaust gas from exhaust passage 48 to intake passage 44 via EGR passage 140. The amount of EGR provided to intake passage 44 may be varied by controller 12 via EGR valve 142. Further, an EGR sensor 144 may be arranged within the EGR passage and may provide an indication of one or more of pressure, temperature, and concentration of the exhaust gas. Under some conditions, the EGR system may be used to regulate the temperature of the air and fuel mixture within the combustion chamber, thus providing a method of controlling the timing of ignition during some combustion modes. Further, during some conditions, a portion of combustion gases may be retained or trapped in the combustion chamber by controlling exhaust valve timing, such as by controlling a variable valve timing mechanism.

Controller 12 is shown in FIG. 1 as a microcomputer, including microprocessor unit 102, input/output ports 104, an electronic storage medium for executable programs and calibration values shown as read only memory chip 106 in this particular example, random access memory 108, keep alive memory 110, and a data bus. Controller 12 may receive various signals from sensors coupled to engine 10, in addition to those signals previously discussed, including measurement of inducted mass air flow (MAF) from mass air flow sensor 120; engine coolant temperature (ECT) from temperature sensor 112 coupled to cooling sleeve 114; a profile ignition pickup signal (PIP) from Hall effect sensor 118 (or other type) coupled to crankshaft 40; throttle position (TP) from a throttle position sensor; and absolute manifold pressure signal, MAP, from sensor 122. Engine speed signal, RPM, may be generated by controller 12 from signal PIP.

Storage medium read-only memory 106 can be programmed with computer readable data representing instructions executable by processor 102 for performing the methods described below as well as other variants that are anticipated but not specifically listed.

As described above, FIG. 1 shows only one cylinder of a multi-cylinder engine, and each cylinder may similarly include its own set of intake/exhaust valves, fuel injector, spark plug, etc.

Figure 2:
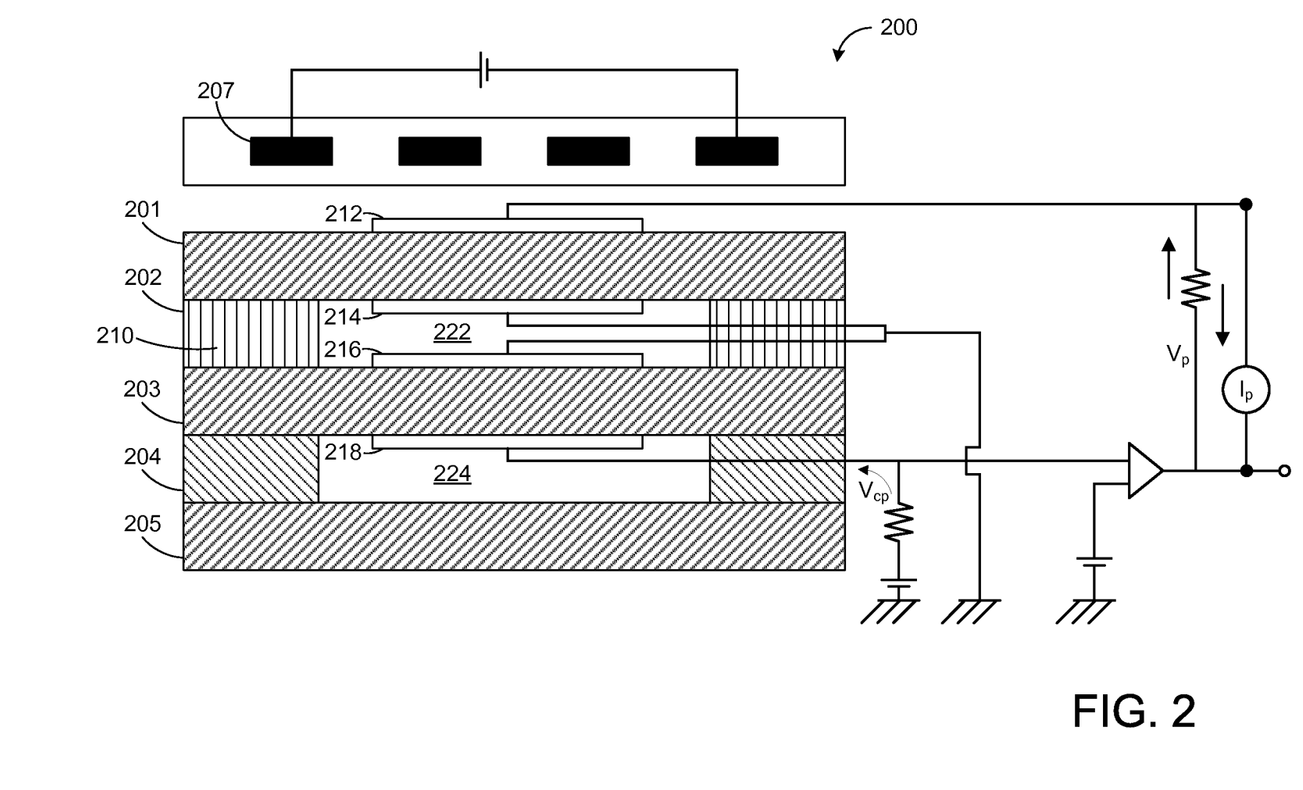
FIG. 2 shows a schematic diagram of an example exhaust gas sensor.

Next, FIG. 2 shows a schematic view of an example embodiment of a UEGO sensor 200 configured to measure a concentration of oxygen ($O_2$) in an exhaust gas stream. Sensor 200 may operate as UEGO sensor 126 of FIG. 1, for example. Sensor 200 comprises a plurality of layers of one or more ceramic materials arranged in a stacked configuration. In the embodiment of FIG. 2, five ceramic layers are depicted as layers 201, 202, 203, 204, and 205. These layers include one or more layers of a solid electrolyte capable of conducting ionic oxygen. Examples of suitable solid electrolytes include, but are not limited to, zirconium oxide-based materials. Further, in some embodiments, a heater 207 may be disposed in thermal communication with the layers to increase the ionic conductivity of the layers. While the depicted UEGO sensor is formed from five ceramic layers, it will be appreciated that the UEGO sensor may include other suitable numbers of ceramic layers.

Layer 202 includes a material or materials creating a diffusion path 210. Diffusion path 210 is configured to introduce exhaust gases into a first internal cavity 222 via diffusion. Diffusion path 210 may be configured to allow one or more components of exhaust gases, including but not limited to a desired analyte (e.g., $O_2$), to diffuse into internal cavity 222 at a more limiting rate than the analyte can be pumped in or out by pumping electrodes pair 212 and 214. In this manner, a stoichiometric level of $O_2$ may be obtained in the first internal cavity 222.

Sensor 200 further includes a second internal cavity 224 within layer 204 separated from the first internal cavity 222 by layer 203. The second internal cavity 224 is configured to maintain a constant oxygen partial pressure equivalent to a stoichiometric condition, e.g., an oxygen level present in the second internal cavity 224 is equal to that which the exhaust gas would have if the air-fuel ratio was stoichiometric. The oxygen concentration in the second internal cavity 224 is held constant by pumping voltage $V_{cp}$. Herein, second internal cavity 224 may be referred to as a reference cell.

A pair of sensing electrodes 216 and 218 is disposed in communication with first internal cavity 222 and reference cell 224. The sensing electrodes pair 216 and 218 detects a concentration gradient that may develop between the first internal cavity 222 and the reference cell 224 due to an oxygen concentration in the exhaust gas that is higher than or lower than the stoichiometric level. A high oxygen concentration may be caused by a lean exhaust gas mixture, while a low oxygen concentration may be caused by a rich mixture.

A pair of pumping electrodes 212 and 214 is disposed in communication with internal cavity 222, and is configured to electrochemically pump a selected gas constituent (e.g., $O_2$) from internal cavity 222 through layer 201 and out of sensor 200. Alternatively, the pair of pumping electrodes 212 and 214 may be configured to electrochemically pump a selected gas through layer 201 and into internal cavity 222. Herein, pumping electrodes pair 212 and 214 may be referred to as an $O_2$ pumping cell.

Electrodes 212, 214, 216, and 218 may be made of various suitable materials. In some embodiments, electrodes 212, 214, 216, and 218 may be at least partially made of a material that catalyzes the dissociation of molecular oxygen. Examples of such materials include, but are not limited to, electrodes containing platinum and/or silver.

The process of electrochemically pumping the oxygen out of or into internal cavity 222 includes applying a voltage $V_p$ across pumping electrode pair 212 and 214. The pumping voltage $V_p$ applied to the $O_2$ pumping cell pumps oxygen into or out of first internal cavity 222 in order to maintain a stoichiometric level of oxygen in the cavity pumping cell. The resulting pumping current $I_p$ is proportional to the concentration of oxygen in the exhaust gas. A control system (not shown in FIG. 2) generates the pumping current signal $I_p$ as a function of the intensity of the applied pumping voltage $V_p$ required to maintain a stoichiometric level within the first internal cavity 222. Thus, a lean mixture will cause oxygen to be pumped out of internal cavity 222 and a rich mixture will cause oxygen to be pumped into internal cavity 222.

It should be appreciated that the UEGO sensor described herein is merely an example embodiment of a UEGO sensor, and that other embodiments of UEGO sensors may have additional and/or alternative features and/or designs.

As elaborated below, the UEGO sensor of FIG. 2 can be advantageously used to estimate an amount of alcohol in the fuel burned in the engine as well as an ambient humidity. In particular, a change in pumping current (delta Ip) output by the sensor at two difference reference voltages is used to determine the amount of oxygen coming from water and/or $CO_2$ dissociation. However, the inventors herein have recognized that the exhaust air-fuel ratio changes the delta Ip signal. This makes it difficult to accurately determine the relation between the delta Ip signal and the amount of water in the exhaust.

Figure 7:
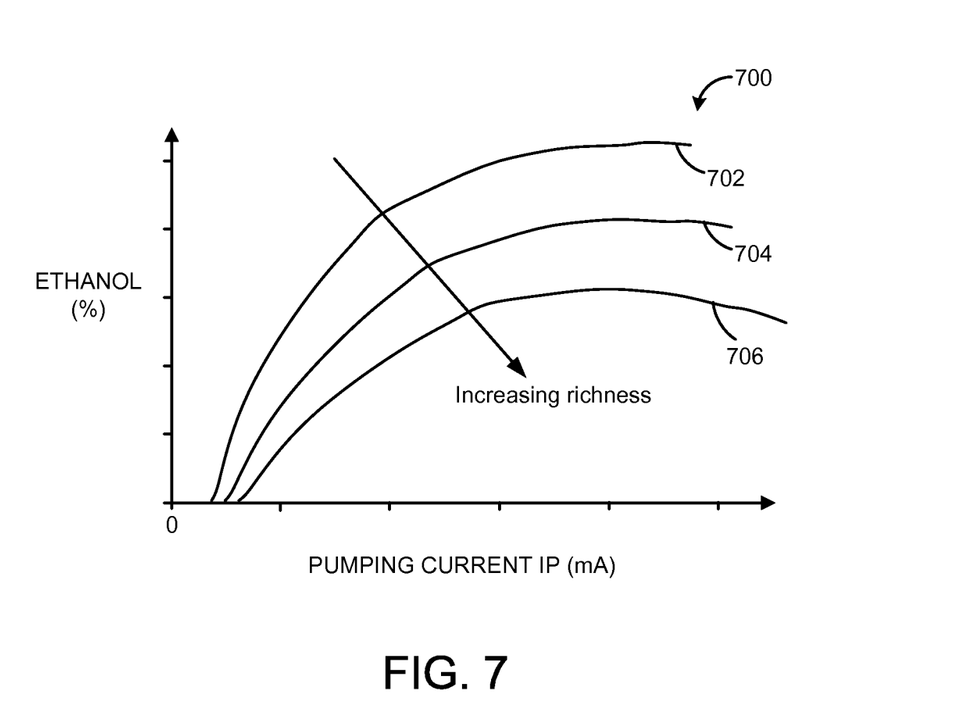
FIG. 7 shows a graph depicting impact of air-fuel ratio and engine temperature on fuel ethanol estimation.

FIG. 7 shows a graph 700 depicting the impact of air-fuel ratio on fuel ethanol estimation. Each of curves 702-706 depicts a relationship between the pumping current output by the sensor and the ethanol content of the burned fuel. Curve 704 shows the relationship at approximately stoichiometric exhaust air-fuel ratio, while curve 702 shows the relationship at a lean air-fuel ratio, and curve 706 shows a rich air-fuel ratio. As the richness of the exhaust air-fuel ratio exceeds stoichiometry, the pumping current output by the sensor decreases for a given fuel ethanol concentration. If the uncorrected pumping current were used, the ethanol concentration estimated would be higher than actually present. For example, the delta Ip when operating with ethanol fuel E45 is expected to be less than the delta Ip for E55. However, in the presence of rich exhaust air-fuel ratio, the delta Ip estimated with E45 may be higher than that for E55. Therefore, the inventors have recognized that by learning the actual air-fuel ratio and correcting the delta Ip for the variation in air-fuel ratio from a target or threshold air-fuel ratio (such as a difference from stoichiometry), a more accurate delta Ip can be determined and the ethanol (or humidity) estimation can be performed more reliably.

Figure 3:
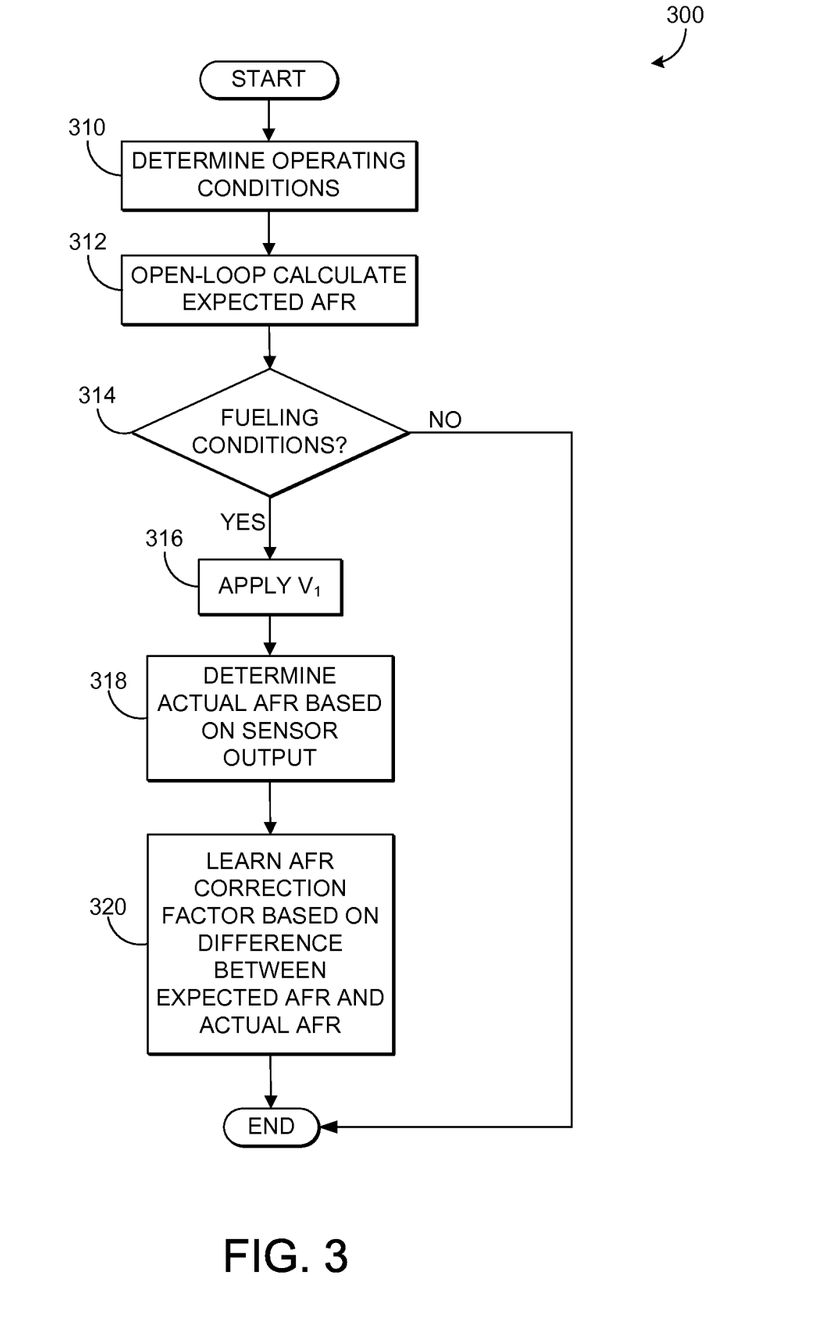
FIG. 3 shows a flow chart illustrating a routine for learning an air-fuel ratio correction factor.
Figure 4:
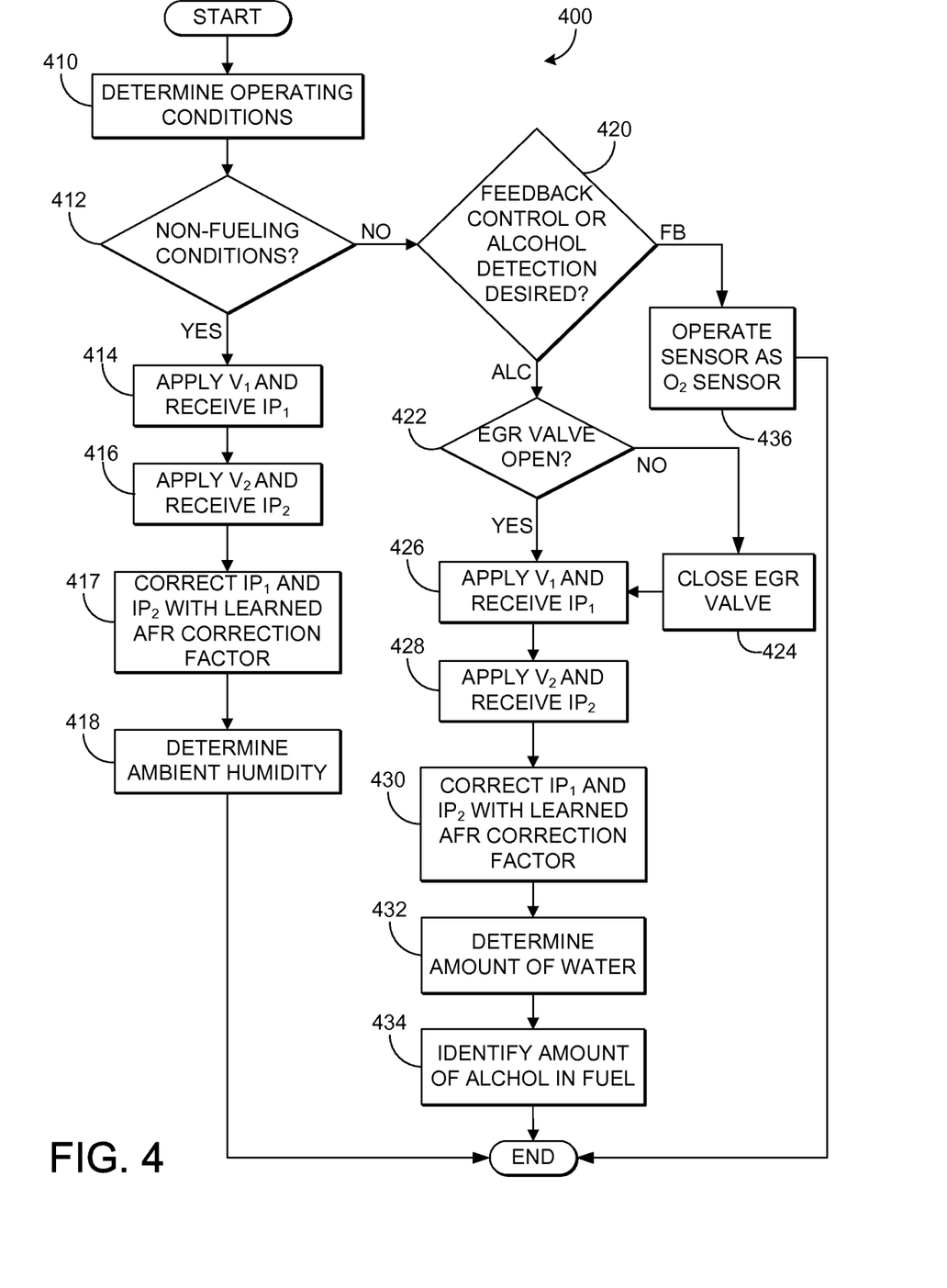
FIG. 4 shows a flow chart illustrating a routine for accurately estimating an amount of alcohol in fuel as well as an ambient humidity with an exhaust gas sensor, while correcting for effects of air-fuel ratio variation.
Figure 5:
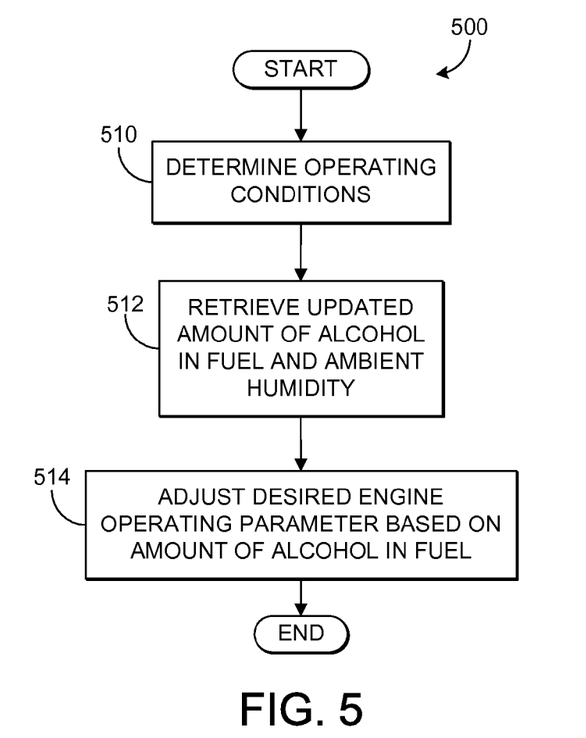
FIG. 5 shows a flow chart illustrating a routine for controlling an engine based on an exhaust gas sensor.

FIGS. 3-5 show flow charts illustrating routines for an engine system which includes an exhaust gas sensor, such as the exhaust gas sensor 200 described above with reference to FIG. 2. In particular, FIG. 3 shows a routine for learning an air-fuel ratio correction factor. FIG. 4 shows a routine for accurately estimating an amount of alcohol in fuel as well as an ambient humidity with the exhaust gas sensor, while correcting for effects of air-fuel ratio variation based on the air-fuel ratio correction factor learned in FIG. 3. For example, under a first engine fueling condition, a first voltage is applied such that the air-fuel ratio correction factor may be learned from the exhaust gas sensor output. Under a second engine fueling condition following the first fueling condition, sequentially applying first and second voltages to the sensor and correcting the sensor outputs such that fuel alcohol content may be determined based on the sensor. Finally, under a third engine non-fueling condition, alternating between applying the first and second voltages and correcting the sensor outputs such that ambient humidity may be determined based on the sensor. FIG. 5 shows a routine for controlling an engine based on the estimated amounts of ambient humidity and fuel alcohol content from the exhaust gas sensor. By determining the air-fuel ratio correction factor (e.g., an error of the air-fuel ratio sensor) and applying it to exhaust gas sensor output, ambient humidity and fuel alcohol content may be more accurately estimated such that the engine system may be controlled more accurately.

Continuing to FIG. 3, a flow chart illustrating a routine 300 for learning an air-fuel ratio correction factor is shown. Specifically, routine 300 learns an error between an expected air-fuel ratio and an actual air-fuel ratio under engine fueling conditions. For example, the expected air-fuel ratio may be determined based on operating parameters, while the actual air-fuel ratio is determined based on output of an exhaust gas sensor, such as the universal exhaust gas oxygen sensor 200 described above with reference to FIG. 2.

At 310, engine operating conditions are determined. Engine operating conditions may include but are not limited to air-fuel ratio, amount of EGR entering the combustion chambers, and fueling conditions, for example.

Once the operating conditions are determined, routine 300 continues to 312 where the expected air-fuel ratio is calculated in open-loop manner. For example, the expected air-fuel ratio may be calculated based on operating parameters such as fuel injection and air flow amounts.

At 314, it is determined if the engine is under fueling conditions. For example, it may be determined that the engine is under fueling conditions if fuel is being delivered to at least one cylinder of the engine for combustion. If it is determined that the engine is not under fueling conditions (e.g., the engine is under non-fueling conditions), the routine ends.

On the other hand, if it is determined that the engine is under fueling conditions, the routine proceeds to 316 and a first pumping voltage ($V_1$) is applied to the oxygen pumping cell of the exhaust gas sensor. Application of the first voltage generates an output of the sensor in the form of a first pumping current that is indicative of an amount of oxygen in the sample gas. In this example, because fuel is injected to the engine and combustion is carried out, the first pumping current may be indicative of an amount of oxygen in the exhaust gas. Thus, at 318, the actual air-fuel ratio is determined based on the sensor output (e.g., responsive to application the first pumping voltage).

Once the actual air-fuel ratio is determined, the correction factor is learned at 320 based on a difference between the expected air-fuel ratio (determined at 311) and the actual air-fuel ratio (determined at 318).

In this manner, the air-fuel ratio correction factor may be determined. As such, estimation of exhaust water content and fuel alcohol content may be accurately determined, as described in detail with reference to FIG. 4 below, without requiring the air-fuel ratio to be accurately controlled to a target value.

Continuing to FIG. 4, a flow chart illustrating an estimation routine 400 for an exhaust gas sensor, such as UEGO 200 shown in FIG. 2, is shown. Specifically, routine 400 determines an amount of alcohol in the fuel injected to the engine, and thus the fuel type, based on voltages applied to a pumping cell of the sensor during selected engine fueling conditions and further based on the air-fuel ratio correction factor calculated as described above with reference to FIG. 3.

At 410 of routine 400, engine operating conditions are determined. Engine operating conditions may include but are not limited to air-fuel ratio, amount of EGR entering the combustion chambers, and fueling conditions, for example.

Once the engine operating conditions are determined, routine 400 continues to 412 where it is determined if the engine is under non-fueling conditions. Non-fueling conditions include vehicle deceleration conditions and engine operating conditions in which the fuel supply is interrupted but the engine continues spinning and at least one intake valve and one exhaust valve are operating; thus, air is flowing through one or more of the cylinders, but fuel is not injected in the cylinders. Under non-fueling conditions, combustion is not carried out and ambient air may move through the cylinder from the intake to the exhaust. In this way, a sensor, such as a UEGO sensor, may receive ambient air on which measurements, such as ambient humidity detection, may be performed.

As noted, non-fueling conditions may include, for example, deceleration fuel shut-off (DFSO). DFSO is responsive to the operator pedal (e.g., in response to a driver tip-out and where the vehicle accelerates greater than a threshold amount). DSFO conditions may occur repeatedly during a drive cycle, and, thus, numerous indications of the ambient humidity may be generated throughout the drive cycle, such as during each DFSO event. As such, the fuel type may be identified accurately based on an amount of water in the exhaust gas despite fluctuations in humidity between drive cycles or even during the same drive cycle.

Continuing with FIG. 4, if is determined that the engine is under non-fueling conditions such as DFSO, routine 300 continues to 414 where a first pumping voltage ($V_1$) is applied to the oxygen pumping cell of the exhaust gas sensor and a first pumping current ($I_{p1}$) is received. The first pumping voltage may have a value such that oxygen is pumped from the cell, but low enough that oxygen compounds such as $H_2O$ (e.g., water) are not dissociated (e.g., $V_1$=450 mV). Application of the first voltage generates an output of the sensor in the form of the first pumping current ($I_{p1}$) that is indicative of the amount of oxygen in the sample gas. In this example, because the engine is under non-fueling conditions, the amount of oxygen may correspond to the amount of oxygen in the fresh air surrounding the vehicle.

Once the amount of oxygen is determined, routine 400 proceeds to 416 where a second pumping voltage ($V_2$) is applied to the oxygen pumping cell of the sensor and a second pumping ($I_{p2}$) current is received. The second voltage may be greater than the first voltage applied to the sensor. In particular, the second voltage may have a value high enough to dissociate a desired oxygen compound. For example, the second voltage may be high enough to dissociate $H_2O$ molecules into hydrogen and oxygen (e.g., $V_2$=1.1 V). Application of the second voltage generates the second pumping current ($I_2$) that is indicative of the amount of oxygen and water in the sample gas. It will be understood that the term "water" in the "amount of oxygen and water" as used herein refers to the amount of oxygen from the dissociated $H_2O$ molecules in the sample gas.

At 417, the first pumping current and the second pumping current are corrected with a learned air-fuel ratio correction factor. For example, the learned air-fuel ratio correction may be determined at 320 of routine 300 described above with reference to FIG. 3.

The ambient humidity (e.g., absolute humidity of the fresh air surrounding the vehicle) may be determined at 418 of routine 400 based on the first pumping current, the second pumping current, and the air-fuel ratio correction factor. For example, the first pumping current may be subtracted from the second pumping current to obtain a value indicative of the amount of oxygen from dissociated water molecules (e.g., the amount of water) in the sample gas. This value may be proportional to the ambient humidity. The ambient humidity value may then be corrected based on the air-fuel ratio correction factor.

On the other hand, if it is determined that the engine is not under non-fueling conditions, routine 400 of FIG. 4 moves to 420 where is it determined if feedback air-fuel ratio control based on the sensor, or alcohol detection by the sensor, is desired or to be carried out. The selection may be based on operating conditions, such as a duration since a last determination of alcohol, or whether closed loop air-fuel ratio control is enabled. For example, if feedback air-fuel ratio control is disabled, the routine may continue to determine alcohol content, whereas if feedback air-fuel ratio is commanded or enabled, the routine may continue to perform such feedback air-fuel ratio control (without determining alcohol content).

Additionally, in an alternative embodiment, even when feedback air-fuel control is to be carried out, a first oxygen sensor (e.g., a first UEGO sensor) may be used for feedback control, and a second oxygen sensor (e.g., a second UEGO sensor) may be used for determining the fuel alcohol amount. For example, if the engine has two cylinder banks, each with an exhaust UEGO sensor, one UEGO sensor may be used to control the air-fuel ratio of each bank (even though the sensor does not experience exhaust gas from one of the banks) on the assumption that the sensor is at least indicative of the air-fuel ratio of both banks, whereas the UEGO of the other bank is operated to determine fuel alcohol content. Alternatively, the first UEGO sensor may be upstream of the second UEGO sensor in the same exhaust stream. Again, the engine air-fuel ratio may be controlled by adjusting fuel injection based on the upstream UEGO, and the downstream UEGO may be used to measure fuel alcohol content. Thus, in one example, a method may be provided for an engine with a first and second UEGO sensor, where during selected engine fueling conditions, alternating first and second voltages are applied to the first UEGO sensor (and a fuel alcohol amount is determined based on the sensor outputs resulting form the first and second voltages), and at the same time, the fuel injection into the engine is adjusted to maintain a desired air-fuel ratio based on feedback from the second UEGO sensor. Such operation may then be switched between the first and second UEGO sensors in order to monitor whether proper determination of fuel alcohol content has been achieved, and thus to monitor performance of the first and/or second UEGO sensor in identifying fuel alcohol content.

Returning to FIG. 4, if it is determined that feedback control is desired, routine 400 moves to 436 and the sensor is operated as an oxygen (e.g., $O_2$) sensor to determine an oxygen concentration and/or air-fuel ratio of the exhaust gas and the routine ends.

If alcohol detection is desired, routine 400 proceeds to 422 where it is determined if the exhaust gas recirculation (EGR) valve is open. If it is determined that the EGR valve is open, routine 400 moves to 424 and the EGR valve is closed. Once the EGR valve is closed at 424 or if it is determined that the EGR valve is closed at 422, and thus the amount of EGR entering the combustion chamber is substantially zero, routine 400 proceeds to 326 where a first pumping voltage ($V_1$) is applied to the exhaust gas sensor and a first pumping current ($I_{p1}$) is received. As at 414, the first pumping voltage may pump oxygen from the oxygen pumping cell, but may have a low enough valve so as to not dissociate water (e.g., $H_2O$) molecules in the pumping cell (e.g., $V_1$=450 mV). In some examples, the first pumping voltage applied to the sensor at 426 may be the same as the first pumping voltage applied to the sensor at 414. When the first voltage is applied to the pumping cell, the first pumping current ($I_{p1}$) is generated. In this example, because fuel is injected to the engine and combustion is carried out, the first pumping current may be indicative of an amount of oxygen in the exhaust gas.

At 428 of routine 300, a second pumping voltage ($V_2$) is applied to the pumping cell of the exhaust gas sensor and a second pumping current ($I_{p2}$) is received. As above, the second pumping voltage may be greater than the first pumping voltage, and the second voltage may be high enough to dissociate oxygen compounds such as water molecules. Application of the second pumping voltage across the oxygen pumping cell generates the second pumping current ($I_{p2}$). The second pumping current may be indicative of an amount of oxygen and water in the sample gas (e.g., oxygen that already exists in the sample gas plus oxygen from water molecules dissociated when the second pumping voltage is applied).

At 430, the first pumping current and the second pumping current are corrected with a learned air-fuel ratio correction factor. For example, the learned air-fuel ratio correction may be determined at 320 of routine 300 described above with reference to FIG. 3.

Once the first and second pumping currents are generated, an amount of water in the sample gas may be determined at 432 of routine 400 in FIG. 4. For example, the first pumping current may be subtracted from the second pumping current, and then corrected based on the air-fuel ratio correction factor to determine a value that corresponds to an amount of water.

Figure 6:
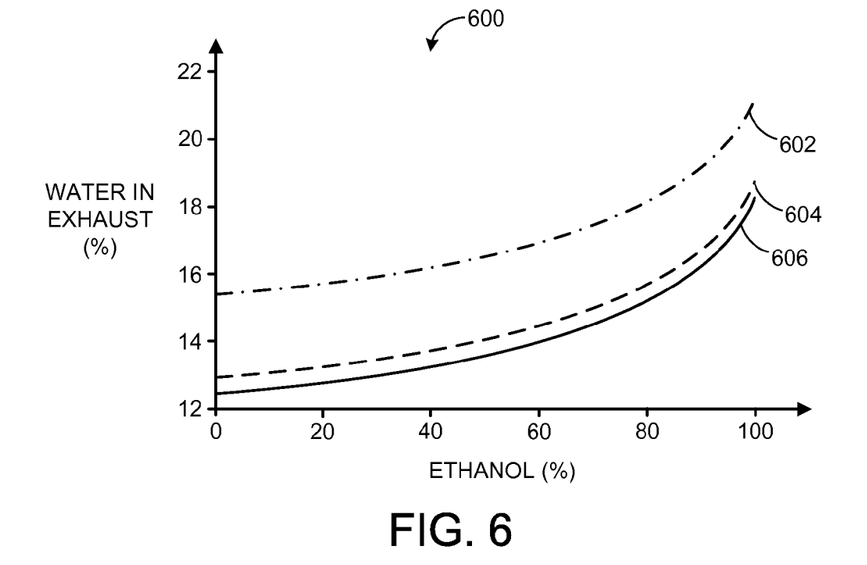
FIG. 6 shows a graph demonstrating a relationship between water in exhaust gas and ethanol.

Finally, the amount of alcohol in the fuel, and thus the fuel type, may be identified at 434. For example, the amount of water in the exhaust gas may be proportional to an amount of alcohol (e.g., a percent of ethanol) in the fuel injected to the engine. Because ambient humidity may also contribute to an amount of water in the exhaust gas, the ambient humidity determined at 418 may be subtracted from the amount of water determined at 430. In some embodiments, the computer readable storage medium of the control system receiving communication from the sensor may include instructions for identifying the amount of alcohol. For example, graph 600 in FIG. 6 shows examples of the relationship between water after combustion (e.g., percent of water in exhaust gas) and the percent of ethanol in the fuel that may be stored on the computer readable storage medium in the form of a lookup table, for example. The solid curve 606 of graph 600 shows the percent of water in the exhaust gas when there is zero ambient humidity. The dashed curve 604 and dashed/dotted curve 602 show the percent of water in the exhaust gas when there is 0.5 mol % and 3.5 mol % water, respectively, due to ambient humidity. As demonstrated by graph 600, as the amount of ethanol in the fuel increases, the amount of water in the exhaust gas increases.

Thus, based on sensor outputs (e.g., pumping currents) generated responsive to voltages applied sequentially to the oxygen pumping cell of the exhaust gas sensor during engine fueling and non-fueling conditions and the air-fuel ratio correction factor, amounts of water in the exhaust gas may be determined. In this manner, an accurate indication of the amount alcohol (e.g., percent ethanol) in the fuel may be identified. Further, once the fuel type is determined, various engine operating parameters may be adjusted to maintain engine and/or emissions efficiency, as will be described in detail below.

Referring now to FIG. 5, a flow chart depicting a general control routine 500 for adjusting engine operating parameters based on an amount of alcohol in fuel injected to the engine is shown. Specifically, one or more engine operating parameters may be adjusted corresponding to a change in the amount of alcohol in the fuel. For example, fuels containing different amount of alcohol may have different properties such as viscosity, octane number, latent enthalpy of vaporization, etc. As such, engine performance, fuel economy, and/or emissions may be degraded if one or more appropriate operating parameters are not adjusted.

At 510 of routine 500, engine operating conditions are determined. Engine operating conditions may include, for example, air-fuel ratio, fuel injection timing, and spark timing. For example, the ratio of air to fuel which is stoichiometric may vary for varying types (e.g., 14.7 for gasoline, 9.76 for E85) and fuel injection timing and spark timing may need to be adjusted based on the fuel type.

Once the operating conditions are determined, an updated amount of alcohol in the fuel mixture and the ambient humidity are determined at 512 of routine 500. As described above, the fuel type may be determined based on outputs from an exhaust gas sensor such as a UEGO sensor. After the fuel type is known, routine 500 proceeds to 514 where, under selected operating conditions such as cold start or transient fueling conditions, one or more desired operating parameters are adjusted based on the amount of alcohol in the fuel. For example, the system may adjust the stoichiometric air-fuel ratio based on the amount of alcohol in the fuel. Further, feedback air-fuel ratio control gains may be adjusted based on the amount of alcohol in the fuel. Further still, the desired air-fuel ratio during cold starting may be adjusted based on the amount of alcohol in the fuel. Further still, spark angle (such as spark retard) and/or boost levels may be adjusted based on the amount of alcohol in the fuel.

In some embodiments, for example, the timing and/or amount of the fuel injection in one or more cylinders may be adjusted. For example, if it is determined that the amount of alcohol in the fuel is increased (e.g., from 10% ethanol to 30% ethanol) during cold start conditions, the amount of fuel injected to the engine may be increased.

As another example, spark timing may be adjusted based on the detected amount of alcohol in the fuel. For example, if the detected percentage of alcohol is lower than previously detected (e.g., from 85% ethanol to 50% ethanol), the spark timing may be retarded in order to achieve a higher engine output or boost without knock.

Thus, various engine operating parameters may be adjusted during selected operating conditions based on a detected amount of alcohol in the fuel injected to the cylinders of the engine. In this manner, engine and/or emissions efficiency as well as fuel economy may be maintained or improved.

Figure 8:
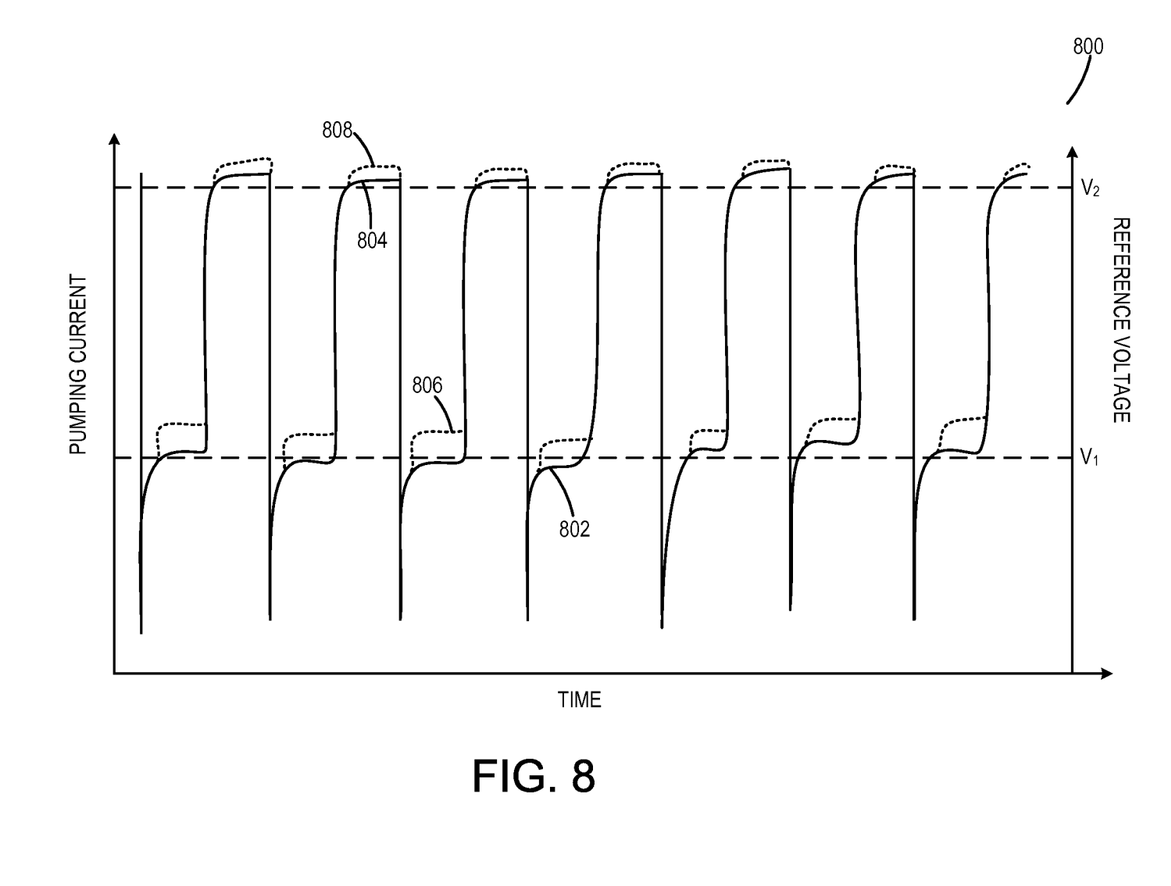
FIG. 8 shows a graph depicting a pumping current signal corrected for air-fuel ratio effects.

FIG. 8 shows a graph 800 depicting a pumping current signal corrected for air-fuel ratio effects. The curve 802 shows a first, uncorrected pumping current responsive to application of a first voltage ($V_1$) and the curve 804 shows a second, uncorrected pumping current responsive to application of a second, higher voltage ($V_2$). The dashed curve 806 shows the first pumping current corrected based on the air-fuel ratio correction factor. The dashed curve 808 shows the second pumping current corrected based on the air-fuel ratio correction factor. As demonstrated by graph 800, the pumping current may be adjusted by the air-fuel ratio correction factor such that the pumping current has an accurate value, even if the air-fuel ratio is different from an expected value.

In this way, the accuracy of exhaust water content estimation and fuel alcohol content determination can be improved without requiring extensive air-fuel ratio control during the estimation. By determining the exhaust air-fuel ratio present at the time of exhaust water content estimation, and correcting an exhaust oxygen sensor output for a difference between the exhaust air-fuel ratio from a target or nominal air-fuel ratio, the impact of a lean or rich exhaust on the sensor measurement can be accounted for. As such, this reduces the need for precisely controlling the air-fuel ratio to the target prior to and during the oxygen sensor operation, and allows the water estimation to be performed without requiring fuel adaptation to be completed. By also using the same exhaust gas oxygen sensor to measure the actual air-fuel ratio, as well as humidity and ethanol content, component reduction benefits are achieved.

Note that the example control and estimation routines included herein can be used with various engine and/or vehicle system configurations. The specific routines described herein may represent one or more of any number of processing strategies such as event-driven, interrupt-driven, multi-tasking, multi-threading, and the like. As such, various acts, operations, or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated acts or functions may be repeatedly performed depending on the particular strategy being used. Further, the described acts may graphically represent code to be programmed into the computer readable storage medium in the engine control system.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and nonobvious combinations and subcombinations of the various systems and configurations, and other features, functions, and/or properties disclosed herein.

The following claims particularly point out certain combinations and subcombinations regarded as novel and nonobvious. These claims may refer to "an" element or "a first" element or the equivalent thereof. Such claims should be understood to include incorporation of one or more such elements, neither requiring nor excluding two or more such elements. Other combinations and subcombinations of the disclosed features, functions, elements, and/or properties may be claimed through amendment of the present claims or through presentation of new claims in this or a related application.

Such claims, whether broader, narrower, equal, or different in scope to the original claims, also are regarded as included within the subject matter of the present disclosure.

The invention claimed is:

1. A method, comprising:
during a first engine fueling condition,
applying a first voltage to an exhaust gas sensor; and
learning an air-fuel ratio correction factor based on a sensor output; and
during a second engine fueling condition following the first condition,
alternating between applying first and second voltages to the sensor; and
estimating an injected fuel alcohol content based on sensor outputs at the first and second voltages and the learned correction factor.

2. The method of claim 1, wherein learning the correction factor includes learning the correction factor based on a difference between an expected air-fuel ratio and an actual air-fuel ratio, the actual air-fuel ratio based on the sensor output.

3. The method of claim 2, wherein the first voltage is less than the second voltage, and the second voltage dissociates water molecules and the first voltage does not.

4. The method of claim 3, wherein the sensor outputs at the first and second voltages include a first pumping current generated responsive to applying the first voltage and a second pumping current generated responsive to applying the second voltage.

5. The method of claim 4, wherein the first pumping current is indicative of an amount of oxygen and the second pumping current is indicative of an amount of oxygen and water.

6. The method of claim 5, wherein an amount of water is proportional to the amount of alcohol in fuel injected to the engine, and the amount of alcohol is a percent ethanol.

7. The method of claim 1, further comprising, during a third engine non-fueling condition following the first condition, alternating between applying the first and second voltages to the exhaust gas sensor, and generating an indication of ambient humidity based on the sensor outputs at the first and second voltages and the learned correction factor.

8. The method of claim 7, wherein the third engine non-fueling condition includes a deceleration fuel cut-off wherein at least one intake valve and one exhaust valve of the engine are open.

9. The method of claim 1, wherein the exhaust gas sensor is a universal exhaust gas oxygen sensor.

10. A method for an engine, comprising:
applying a first, lower voltage to an exhaust gas sensor during fueled engine operation to learn an error between an expected air-fuel ratio and an actual air-fuel ratio;
after learning the error,
sequentially applying each of the first voltage and a second, higher voltage to the sensor during fueled engine operation;
correcting sensor outputs at the first and second voltages based on the learned error; and
estimating an ethanol content of burned fuel based on the corrected sensor outputs.

11. The method of claim 10, wherein correcting sensor outputs includes correcting a first pumping current output by the sensor responsive to application of the first voltage with the learned error, and correcting a second pumping current output by the sensor responsive to application of the second voltage with the learned error.

12. The method of claim 11, wherein estimating an ethanol content includes estimating a water content of delivered fuel based on a difference between the corrected first pumping current and the corrected second pumping current, and inferring the ethanol content of the fuel based on the estimated water content.

13. The method of claim 12, further comprising, sequentially applying each of the first and second voltage to the exhaust gas sensor during unfueled engine operation; correcting sensor outputs at the first and second voltages based on the learned error; and estimating an ambient humidity based on the corrected sensor outputs.

14. The method of claim 13, further comprising, adjusting EGR flow based on one or more of the estimated ambient humidity and an estimated fuel alcohol content.

15. The method of claim 10, wherein applying the first voltage to learn the error includes open-loop calculating the expected air-fuel ratio based on fuel injection and air flow amounts, measuring the actual air-fuel ratio based on an output of the sensor upon applying the first voltage, and learning the error based on a difference between the expected air-fuel ratio and the actual air-fuel ratio.

16. The method of claim 15, wherein the output of the exhaust gas sensor upon applying the first voltage is a sensor pumping current.

17. A system for controlling an engine in a flex-fuel vehicle, the system comprising:
an exhaust manifold including an exhaust gas oxygen sensor; and
a controller including a computer readable storage medium comprising instructions for:
during selected engine fueling conditions,
applying a first, lower voltage to the sensor and receiving a first pumping current output from the sensor, the first pumping current indicative of an amount of oxygen;
estimating an exhaust air-fuel ratio based on the first pumping current;
learning a correction factor based on the estimated exhaust air-fuel ratio relative to an expected air-fuel ratio;

after the learning,
applying a second, higher voltage to the sensor and receiving a second pumping current output from the sensor, the second pumping current indicative of an amount of oxygen and water; and
identifying an amount of ethanol in fuel burned in the engine based on the first and second pumping currents and the correction factor.

18. The system of claim 17, wherein the identifying includes applying the correction factor to each of the first and second pumping currents output by the exhaust gas oxygen sensor, and calculating the amount of ethanol based on a difference between the corrected first and second pumping currents.

19. The system of claim 18, wherein the controller includes further instructions for correcting the amount of ethanol in fuel burned in the engine based on ambient humidity, the ambient humidity based on an output of the sensor upon applying the first voltage during engine non-fueling conditions.

20. The system of claim 19, wherein the controller includes further instructions for,
adjusting an engine operating parameter based on the amount of ethanol in the fuel and the ambient humidity, the engine operating parameter including one or more of an EGR flow, spark timing, and a fuel injection amount.

* * * * *